(12) United States Patent
Takemoto

(10) Patent No.: US 6,630,676 B2
(45) Date of Patent: Oct. 7, 2003

(54) X-RAY IMAGE TAKING APPARATUS WITH PLANE TYPE RADIATION DETECTOR UNIT

(75) Inventor: Takayuki Takemoto, Joyo (JP)

(73) Assignee: Shimadzu Corporation, Kyoto (JP)

( * ) Notice: Subject to any disclaimer, the term of this patent is extended or adjusted under 35 U.S.C. 154(b) by 122 days.

(21) Appl. No.: 09/871,670

(22) Filed: Jun. 4, 2001

(65) Prior Publication Data

US 2002/0017610 A1 Feb. 14, 2002

(30) Foreign Application Priority Data

Aug. 7, 2000 (JP) ........................................ 2000-238234

(51) Int. Cl.⁷ .................................................. A61B 6/00
(52) U.S. Cl. .............................. 250/370.09; 250/370.07
(58) Field of Search ........................ 250/370.09, 370.07, 250/370.11, 208.1; 378/54, 55, 98.8, 98, 98.2, 62; 600/407, 425, 503

(56) References Cited

U.S. PATENT DOCUMENTS

| | | | | |
|---|---|---|---|---|
| 4,383,327 A | * | 5/1983 | Kruger | 378/19 |
| 5,287,546 A | * | 2/1994 | Tesic et al. | 378/54 |
| 5,990,990 A | * | 11/1999 | Crabtree | 349/74 |
| 6,121,620 A | * | 9/2000 | Tashiro et al. | 250/370.11 |
| 6,155,713 A | * | 12/2000 | Watanabe | 378/197 |
| 6,239,439 B1 | * | 5/2001 | Itabashi et al. | 250/370.11 |
| 6,285,739 B1 | * | 9/2001 | Rudin et al. | 378/98.8 |
| 6,323,490 B1 | * | 11/2001 | Ikeda et al. | 250/370.09 |

* cited by examiner

Primary Examiner—Constantine Hannaher
Assistant Examiner—Otilia Gabor
(74) Attorney, Agent, or Firm—Kanesaka & Takeuchi

(57) ABSTRACT

In a plane type radiation detector unit, a rotating shaft is provided on one end side of the detector unit and is attached to a fluoroscopic radiographing stand to hold the detector unit so that the detector unit can be rotated around the rotating shaft by 90° to widen a space in front of an object or patient to be tested. A plurality of slide electrodes is disposed on the rotating shaft to input or output signals to or from the detector unit, or to supply a power source. A detecting portion of the detector unit includes an X-ray converting layer, an active matrix board, a gate circuit portion and a reading circuit portion. The detecting portion is controlled by a control circuit portion to read pixel signals of the detecting portion to the reading circuit portion and send out data to an outside through the slide electrodes. Also, by providing a communication circuit portion for sending or receiving radio signals from the outside, data can be sent to the outside by radio signals through a non-contact I/O device. Thus, the plane type radiation detector unit can be miniaturized and made light in weight without using a connector and a cable, and moreover, a space in front of the object can be widened.

7 Claims, 5 Drawing Sheets

X-RAY IMAGE TAKING APPARATUS WITH PLANE TYPE RADIATION DETECTOR UNIT

BACKGROUND OF THE INVENTION AND RELATED ART STATEMENT

The invention relates to an X-ray image taking apparatus, more specifically, a mechanism for attaching a plane type radiation detector unit to a C-arm type diagnostic apparatus or fluoroscopic radiographing stand, and input/output (hereinafter referred to as "I/O") cables of a signal and a power source thereof.

With a spread of a digital radiographing (hereinafter referred to as "DR") apparatus, its clinical use has been extended on various fields from an alimentary canal examination to an interventional radiology (hereinafter referred to as "IVR") for a non-blood vessel system and a simple digital subtraction angiography (hereinafter referred to as "DSA").

In addition to the general fluoroscopic radiographing stand, there is an IVR-digital correspondence type fluoroscopic radiographing stand equipped with a C-arm, wherein a digital image processing device is made small in size and high in performance; an operation ability with an X-ray high voltage device is improved; an image intensifier (hereinafter referred to as "I.I.") has a high image quality and a lower distortion; and transfer and preservation of a full digital image are contrived by employing a 4 million pixel CCD camera of a high density resolving power.

FIG. 3 shows a C-arm type X-ray image taking apparatus wherein a TV camera 19 using CCD and an I.I. 18 are provided on a C-arm 14 rotated around a body axis of an object or patient 9 to face an X-ray tube 12 sandwiching therebetween a top board 10, on which the object 9 to be tested is received. In order to provide fluoroscopy or radiograph with X-rays from various angles with respect to the whole body of the object 9, the I.I. 18 and the X-ray tube 12 are rotated in the C directions around the body axis of the object 9 by the C-arm 14, and moved parallel in the A directions, i.e. head-feet directions of the object 9 along a height direction moving guide 15. The I.I. 18 is moved in the D directions on the supporting plate 17 so that the I.I. 18 can be moved to and from the object 9. Also, the I.I. 18 and the X-ray tube 12 can be rotated around the supporting point of the C-arm 14 in the directions of the head-feet of the object 9. The top board 10 can be rotated in the B directions by a rising-falling C-arm 13. As described above, the fluoroscopic radiographing positions can be taken with various angles without moving the object 9.

In the X-ray image taking apparatus using the I.I. 18, since the I.I. 18 is large, when an operator operates the apparatus in the vicinity of the object 9 and when the evacuation is required, the I.I. 18 is moved in a vertical direction.

Recently, in place of the I.I. 18, a plane type radiation detector has been applied to the X-ray image taking device. The plane type radiation detector is normally formed of an X-ray converting film for converting X-rays into light, photo diode arrays arranged in a matrix shape right under the X-ray converting film; and TFT switches connected to the respective photo diode arrays. The plane type radiation detector has two types. In one type, after X-rays are irradiated, the respective TFT switches are sequentially turned on, so that signal charges accumulated in the respective pixels are read out to form an X-ray image. In the other type, there are provided radiation sensor arrays formed of a converting layer for directly outputting charge signals sensitive to radiation and corresponding to incident amount, and the TFT switches are connected to electrodes arranged in a matrix shape right under the radiation sensor arrays. In use, the respective TFT switches are sequentially turned on, so that signal charges accumulated in the respective pixels are read to form an X-ray image. The latter is explained in the following.

FIG. 4 shows a detector cassette 21, wherein a plane type detecting portion 22, power source 26, control circuit portion 25, gate circuit portion 23, reading circuit portion 24 and image memory 27 are built in, and a connecting terminal 28 for external connection is provided. The gate circuit portion 23 and the reading circuit portion 24 are controlled from an outside at the control circuit portion 25 through the connecting terminal 28, and charge signals accumulated in the condensers of the pixels formed of semiconductors in the detecting portion 22 are read in the reading circuit portion 24 and stored in the image memory 27. Then, the data is transferred outside through the connecting terminal 28. The detector cassette 21 is attached to a detecting portion attaching frame of the X-ray image taking apparatus, and a signal cable is connected to the connecting terminal 28.

FIG. 5 shows a detector cassette 21, wherein a plane type detecting portion 22, power source 26, control circuit portion 25, gate circuit portion 23, reading circuit portion 24, image memory 27 and a communication circuit 29 are built in, and input/output of signals with an outer portion are carried out by a communication circuit through radio signals. The gate circuit portion 23 and reading circuit portion 24 are controlled from the control circuit portion 25 through the communication circuit 29 by radio signals from the outside, and charge signals accumulated in the condensers of the pixels formed of the semiconductors at the detecting portion 22 are read in the reading circuit portion 24 and stored in the image memory 27. Then, if necessary, the data is transferred outside from the communication circuit 29. The detector cassette 21 is simply attached to the detecting portion attaching frame of the X-ray image taking apparatus, and output and input of the signals are carried out by radio signals through the communication circuit 29, so that a connecting cable is not required.

FIG. 6 is a sectional view showing a structure of a pixel 30 for constituting the detecting portion 22 of the plane type radiation detector. The pixel 30 includes an active matrix board, wherein electrode wirings, such as gate line and reading signal line, a thin film transistor TFT 32 and a condenser 38 are formed in an X-Y matrix shape on a glass base board; an X-ray converting layer 37 extending over the substantially whole surface above the active matrix board; a pixel electrode 31 positioned thereunder; and an upper electrode 36 located thereabove.

The X-ray converting layer 37 has good photoconducting characteristics according to the irradiation intensity of X-rays to generate a charge signal. For example, a film having a large area can be formed easily by vapor deposition, and amorphous selenium (hereinafter referred to as "a-Se") or the like formed in a film having a thickness of 300 to 1,200 $\mu$m can be used. The upper electrode 36 of the X-ray converting layer 37 is formed on a surface at the X-ray incident side, and the pixel electrode 31 is formed at a position corresponding to each pixel 30 on a side opposite to the X-ray incident side.

The condenser 38 is connected between the pixel electrode 31 and the ground. Also, a bias voltage is applied to the X-ray converting layer 37 from a bias applying portion, and a charge generated at the X-ray converting layer 37 according to an X-ray irradiation intensity is accumulated in the condenser 38.

The TFT 32 has a signal reading switch function and is arranged in two dimensions every pixel 30. And, the charge signal of the condenser 38 is read out by a switch pulse from a gate line terminal 33a to the reading circuit portion 24 through a reading signal line terminal 34a.

FIG. 7 shows a circuit diagram for explaining operations of the plane type radiation detector. The respective pixels 30 are regularly arranged in the length and width directions on the active matrix board 35. The gate circuit portion 23 is driven by the signal from the control circuit portion 25, and pulse signals G1, G2, G3, . . . are sequentially sent to the gate electrodes of the TFTs 32 connected to the pixel electrodes 31 of the respective pixels 30 from the row direction through the gate lines 33. On the other hand, the reading circuit portion 24 is driven by a signal from the control circuit portion 25, and image charge signals of the respective pixels 30, i.e. R1, R2, R3, . . . are sequentially read from the drain electrodes of the TFTs 32 from the column direction through the reading signal lines 34.

In the conventional plane type radiation detector and X-ray image taking apparatus structured as described above, in case the detector cassette 21 as shown in FIGS. 4 and 5 is attached to the C-arm type X-ray image taking apparatus or the general fluoroscopic radiographing stand, there is a problem such that a large attaching mechanism is required for fastening the detector cassette 21.

Also, a cable for inputting or outputting a signal into or from the detector cassette 21 has to be connected. In the power source built-in type detector cassette 21, since a large battery is required, the cassette 21 becomes heavy, so that the battery having a sufficient power source capacity can not be mounted.

Also, when an examination starts or terminates, in case the object or patient 9 gets on or off the top board 10, a detector system, i.e. detector unit, or I.I. 18 and TV camera 19, physically stands on the way of getting on or off the top board 10 of the object 9. Therefore, it is required to move the C-arm to a position where the C-arm does not bother the object 9 in getting on or off the top board 10, or to move the detector system along the supporting plate 17 located at an end portion of the C-arm 14. Thus, time and labor for moving the detector system are increased.

Also, recently, through the introduction of an ultrasonic wave diagnostic apparatus into an examination room, while observing a fluoroscopic image on an X-ray TV monitor and an ultrasonic wave image on a monitor of the ultrasonic wave diagnostic apparatus, there have been increased an examination and treatment by inserting a needle or the like into the object or patient 9. In case a prob of the ultrasonic wave diagnostic apparatus is operated, the operator inevitably stands near the detector system, i.e. detector unit or I.I. 18 and TV camera 19. In case the fluoroscopy is not carried out, the detector system, i.e. detector unit or I.I. 18 and TV camera 19, interferes with the operation, so that the C-arm has to be evacuated whenever it is not used or returned to the proper position whenever it is used.

In view of the above problems, the present invention has been made, and an object of the invention is to provide a plane type radiation detector unit and an X-ray image taking apparatus, which can be used effectively. Namely, in case the plane type radiation detector is attached to a fluoroscopic radiographing stand of a C-arm type X-ray image taking apparatus or the like, a large attaching frame is not required; when a signal is sent out to or received from the outside, a connector and a cable are not required; it is not required to mount a heavy battery to a detector cassette; in case the object or patient 9 gets on or off the top board 10 when a test starts or terminates, the detector system is located away from the object 9; and further, when the operator carries out the inserting examination or treatment with a prob by using an ultrasonic wave diagnostic apparatus together with the X-ray image taking apparatus, the detector system can be easily evacuated.

Further objects and advantages of the invention will be apparent from the following description of the invention.

SUMMARY OF THE INVENTION

In order to attain the above objects, according to a first aspect of the invention, a plane type radiation detector unit is formed of an X-ray converting layer sensitive to X-rays and outputting a charge signal corresponding to an intensity of incident X-rays; an active matrix board having switching elements arranged in a matrix shape and connected right under the X-ray converting layer; a gate circuit portion for sequentially turning on the respective switching elements through gate lines when the signals are read out; a reading circuit portion for reading charge signals accumulated in the respective pixels through reading signal lines; and a control circuit portion for controlling the gate circuit portion and reading circuit portion. The radiation detector unit includes a rotating shaft provided on one end side thereof.

According to a second aspect of the invention, an X-ray image taking apparatus is equipped with the plane type radiation detector unit having a plurality of slide electrodes disposed on the rotating shaft, and a plurality of slip electrodes contacting the slide electrodes provided to the rotating shaft which supports the plane type radiation detector unit.

According to a third aspect of the invention, the X-ray image taking apparatus equipped with the plane type radiation detector unit includes, in an inner portion of the plane type radiation detector unit, a communication circuit portion for receiving radio control signals from an outside to control the control circuit portion and for sending radio output signals from the reading circuit portion; and a remote control reading portion for receiving radio input signals from or sending radio output signal to the outside through the communication circuit portion.

In the plane type radiation detector unit and the X-ray image taking apparatus structured as described above, the rotating shaft is provided to one end side of the plane type radiation detector unit, and the plural slide electrodes are disposed on the rotating shaft. Also, the plural slip electrodes contacting the slide electrodes are located on a side of the X-ray image taking apparatus for supporting the rotating shaft, and, if necessary, the communicating circuit portion is disposed in the plane type radiation detector unit to receive the radio input signals from or send the radio output signals to the outside.

Since the plane type radiation detector unit is held by the rotating shaft, a large attaching frame is not required. Also, since the input or output of signals from or to the outside is continued by the slide electrode and the slip electrode, connection through a connector and a cable is not required. Also, since a power source can be taken from the slide electrodes, it is not required to mount the heavy battery to the detector cassette. Further, in case the test starts or terminates, when the object to be tested gets on or off the top board of an inspection table, or when an operator operates a probe by using an ultrasonic wave diagnostic apparatus together with the X-ray image taking apparatus to carry out the inserting examination and medical treatment, the detector system can be easily evacuated by rotating the rotating shaft by 90°. Also, if necessary, input or output signals can be received or sent through radio communications between the outside remote control reading portion and the inner communication circuit portion.

DETAILED DESCRIPTION OF PREFERRED EMBODIMENTS

Figure 1:
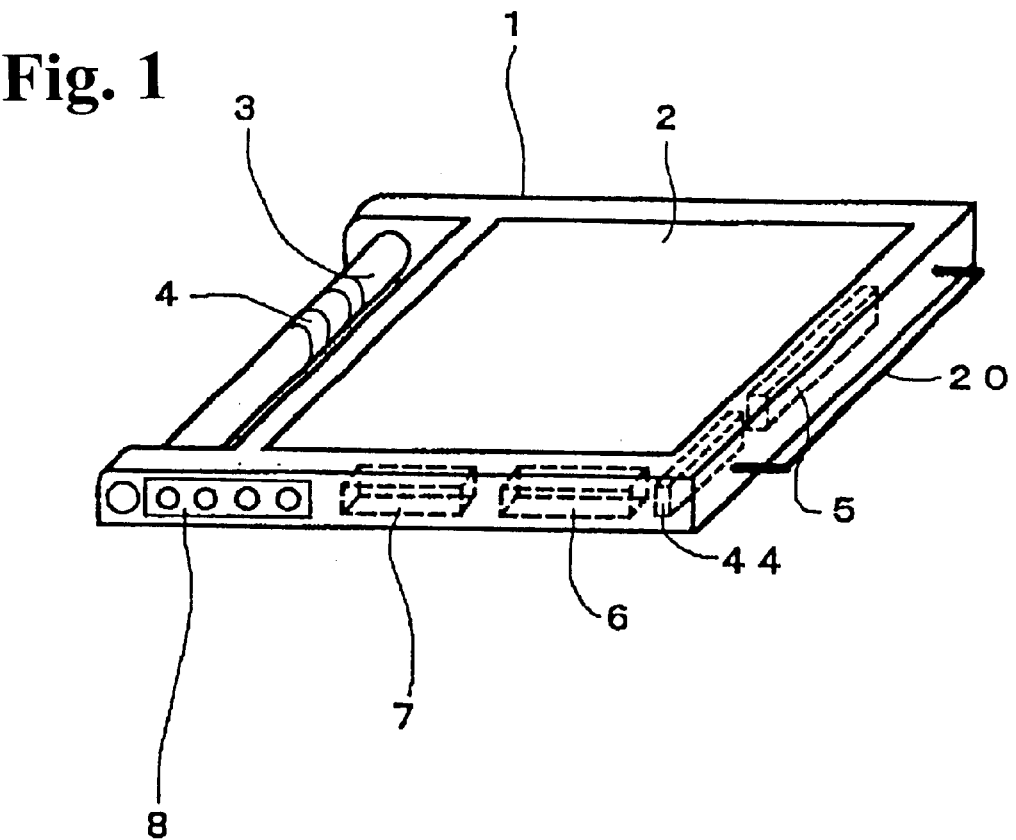
FIG. 1 is a perspective view showing an embodiment of a plane type radiation detector unit according to the invention.
Figure 2:
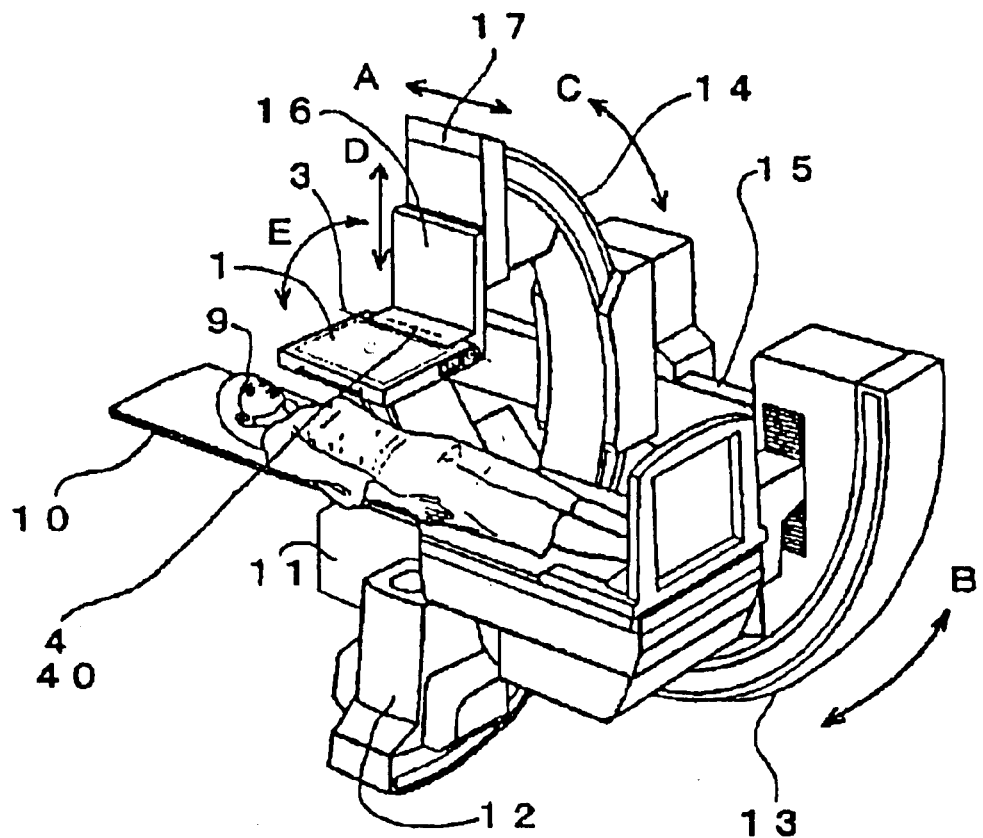
FIG. 2 is a perspective view showing an embodiment of the X-ray image taking apparatus according to the invention.
Figure 2:
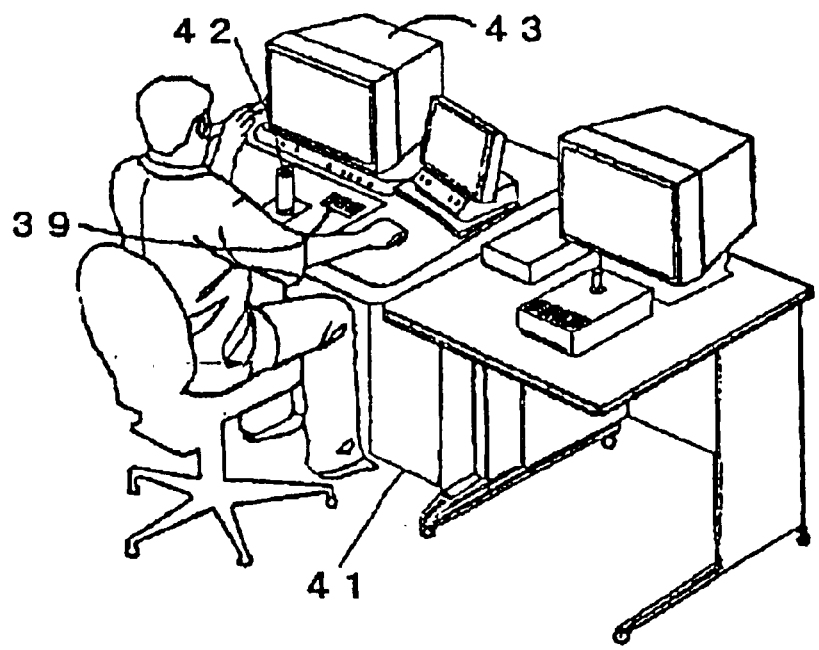

A plane type radiation detector unit and an X-ray image taking apparatus of the present invention are explained with reference to FIGS. 1 and 2. FIG. 1 is a perspective view showing the plane type radiation detector unit of the invention. FIG. 2 is a perspective view showing an external appearance of a C-arm type X-ray image taking apparatus of the invention.

The plane type radiation detector unit includes a detecting portion 2 having an X-ray converting layer for outputting a charge signal sensitive to X-ray and corresponding to intensity of X-ray and an active matrix board including switching elements arranged in a matrix shape directly under the X-ray converting layer; a gate circuit portion 5 for sequentially turning on the respective switching elements through gate lines when signals are read; a reading circuit portion 6 for reading the charge signals accumulated in respective pixels through reading signal lines; a control circuit portion 44 for controlling the gate circuit portion and the reading circuit portion; a rotating shaft 3 for rotatably supporting the detector unit 1 on one end side thereof; a plurality of slide electrodes 4 enabling signals and electric power to be inputted or outputted through electrical contact with the rotating shaft 3; a communication circuit portion 7 for receiving signals from or sending signals to the outside through radio transmission, if necessary; a non-contact I/O device 8 for establishing a communication circuit portion 7; and a handle 20 for easily rotating or holding the detector unit 1.

Figure 7:
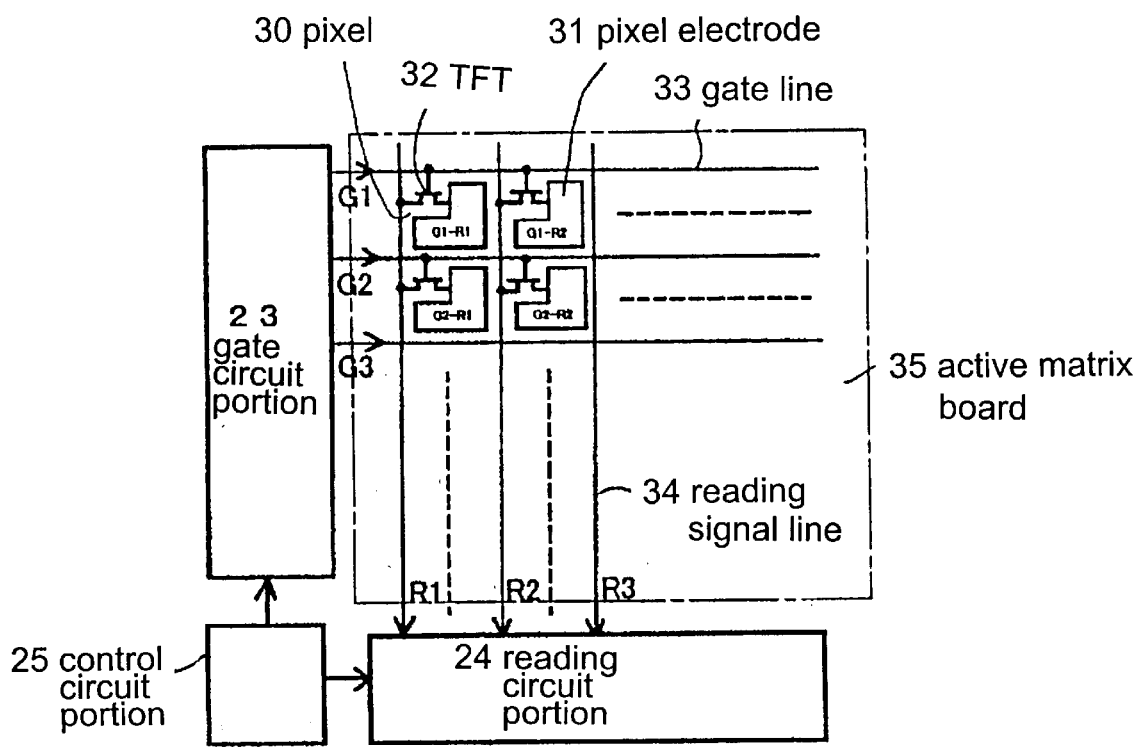
FIG. 7 is a diagram showing a circuit structure of the conventional plane type radiation detector.

Operations of the detecting portion 2 of the detector unit 1 are the same as the operation theory explained with respect to the prior art in FIG. 7. Different points from the prior art reside in that the rotating shaft 3 is provided on one end side of the detector unit 1; the rotating shaft 3 holds the detector unit 1; the rotating shaft 3 is provided with the slide electrodes 4, so that without providing a power source for the detector unit 1 in a detector cassette 21 as in the prior art, the power and the control input and output signals for the detector unit 1 are supplied to an interior from the outside through the slide electrodes 4; and, further, there is provided the communication circuit 7 for allowing signals to be received from or sent to the outside by radio signals, when necessary, so that it is possible to communicate by the non-contact I/O device 8.

The non-contact I/O device 8 having the communication circuit portion 7 is operated by using a wireless communicating device with feeble electric power or an optical communication technique. In one method, image signals are taken out continuously from a transfer register (not shown) disposed to the communication circuit 7, and the communication circuit 7 is controlled by sending the signals as radio waves to a remote control reading portion 39 at an outside, or by receiving radio waves from the remote control reading portion 39 at the outside, through an antenna (not shown) provided at the non-contact I/O device 8 as wireless signals. In the other method, the system uses a light emitting diode or laser diode as a light source to be used for the space-transfer optical communication, and includes a light sending device for forming light beams through a lens to emit into a space by converting information of an electrically signalized X-ray image into intensity or strength of the light, and a light receiving device by focusing the emitted lights to a light receiving surface of a photo-diode through the lens to return the intensity or strength of the light to the original electric signals. The system is provided at the non-contact I/O device 8 and the remote control reading portion 39.

In the latter method, the remote control reading portion 39 may be disposed at a position where the light can be received from or sent to the non-contact I/O device 8, for example, a position which does not prevent the object 9 from being diagnosed on the fluoroscopic radiographing stand by integrally providing in the vicinity of the non-contact I/O device 8 of the detector unit 1. Moreover, as the image signals, a large quantity of data must be transferred, so that a plurality of the non-contact I/O devices 8 is provided to carry out parallel communication. In this case, a signal cable from the remote control reading portion 39 is connected to the control portion 41.

Also, the X-ray image taking apparatus is a C-arm type fluoroscopic radiographing apparatus, and includes an X-ray tube 12; the detector unit 1 attached to one end of the C-arm 14 rotating around a body axis of the object 9 and situated to sandwich a top board 10 for receiving the object 9 thereon together with the X-ray tube 12; the control portion 41 for remote-controlling the fluoroscopic radiographing stand to which the detector unit 1 is attached; an operating handle 42 and a monitor 43 attached to the control portion 41; and the remote control reading portion 39 provided on a control table of the control portion 41 and receiving and sending the signals, by radio waves, from and to the communication circuit portion 7 of the detector unit 1.

In the fluoroscopic radiographing stand of the X-ray image taking apparatus, the detector unit 1 includes slip electrodes 40 contacting the plural slide electrodes 4 provided at the rotating shaft 3, at a side, i.e. supporting plate 16, for supporting the slide electrodes 4, and with a slip-ring mechanism, input/output of the signals from the detector unit 1 and a power supply can be made through the electrodes. Since the detector unit 1 is rotatable around the rotating shaft 3 to retreat in the E direction, a space over the object 9 can be made wide. Also, the detector unit 1 can be moved quickly along a supporting plate 17 attached to one end of the C-arm 14 in the D directions, so that the detector unit 1 can be moved close to or away from the object 9.

Also, the detector unit 1 can be separated from the fluoroscopic radiographing stand at the rotating shaft 3 by loosening a lock of the supporting plate 16 on a side of the fluoroscopic radiographing stand for holding the detector unit 1. The separated detector unit 1 can be used in another fluoroscopic radiographing stand attached thereto.

Figure 3:
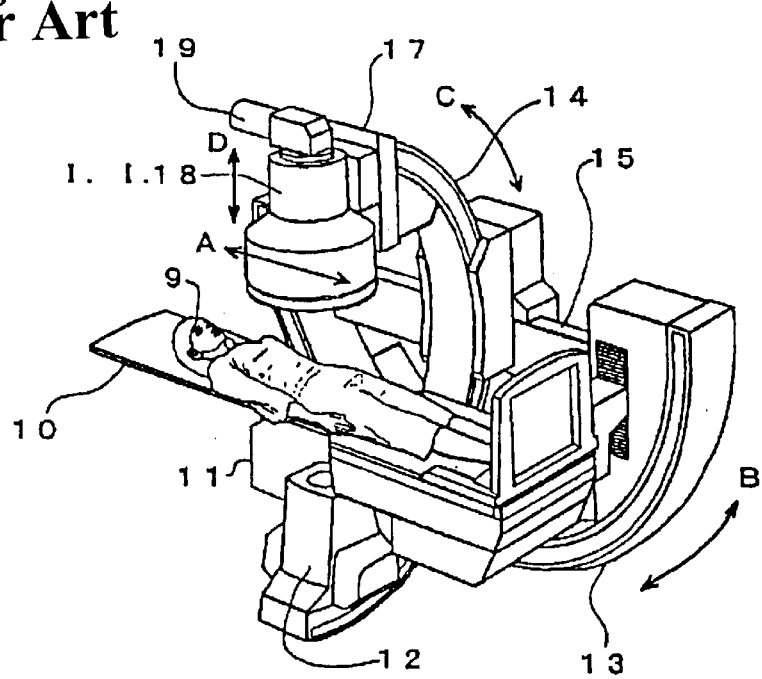
FIG. 3 is a perspective view of a conventional X-ray image taking apparatus.
Figure 4:
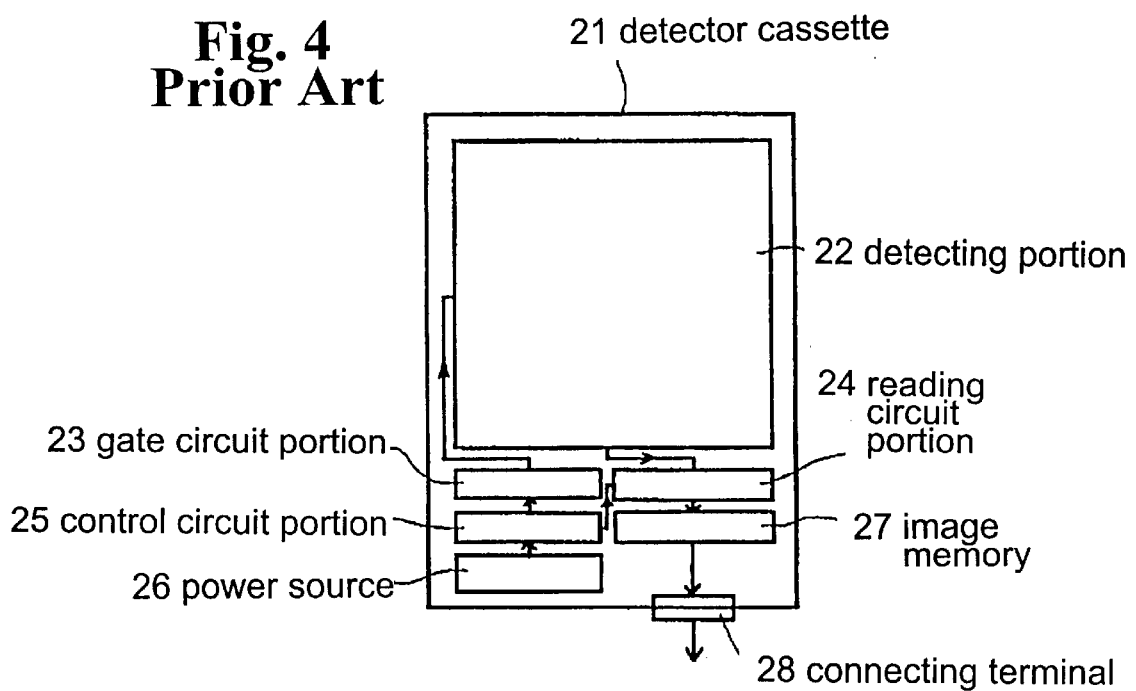
FIG. 4 is a diagram showing a conventional plane type radiation detector cassette.
Figure 5:
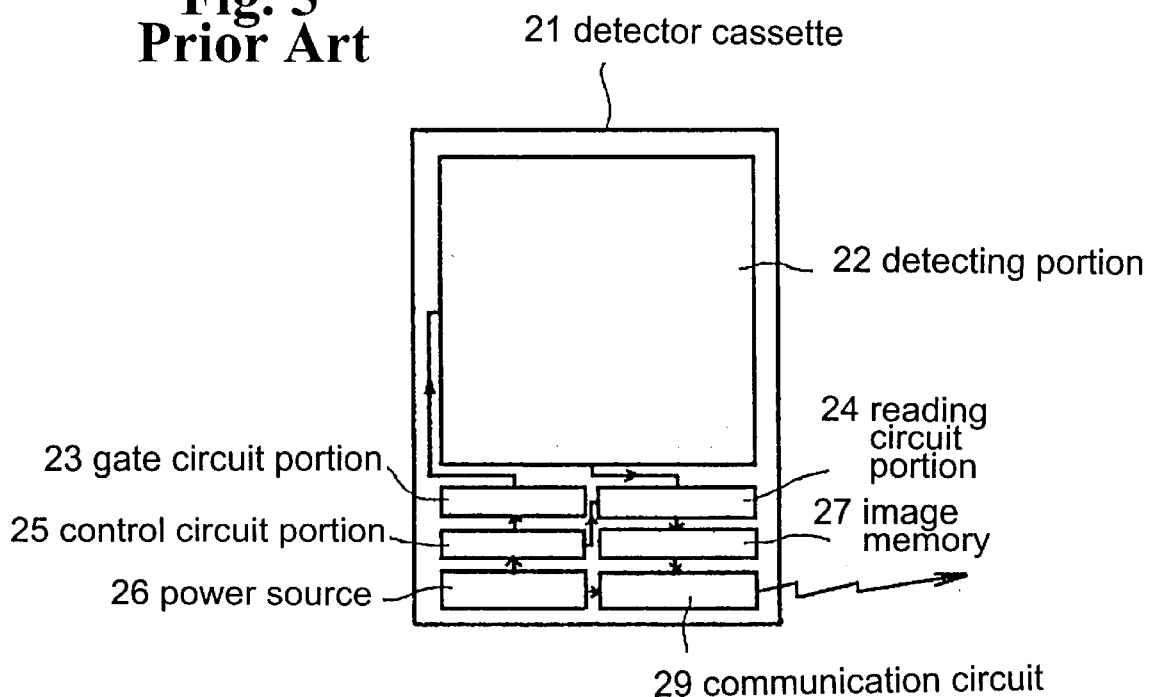
FIG. 5 is a diagram showing another conventional plane type radiation detector cassette.
Figure 6:
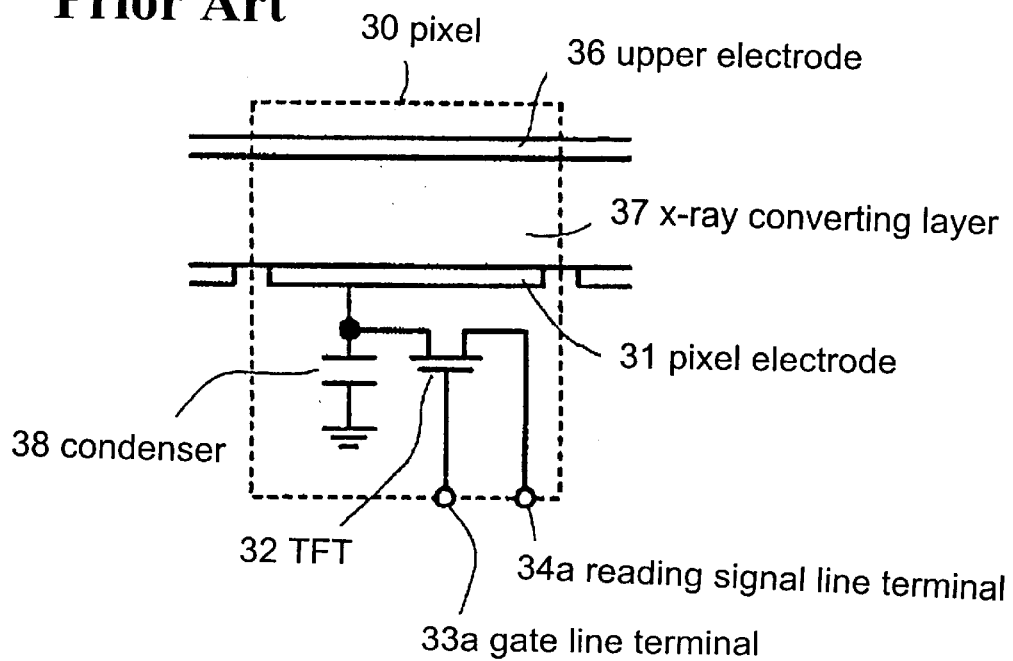
FIG. 6 is a diagram showing a structure of a pixel of the plane type radiation detector.

Also, the detector unit 1 and the X-ray tube 12 are rotated in the C directions around the body axis of the object 9 by the C-arm 14, and moved in the A directions, i.e. parallel to the head-feet directions of the object 9. Also, the detector unit 1 and the X-ray tube 12 can be rotated in the directions of the head-feet of the object 9 around a supporting point of the C-arm 14. The top board 10 can be rotated in the B directions by a rising-falling C-arm 13. When compared with the conventional fluoroscopic radiographing stand provided with the I.I. 18 as shown in FIG. 3, since the detector unit 1 of the invention is small in size and light in weight, radioscopic radiographing positions can be quickly taken with various angles without moving the object 9.

Then, the fluoroscopic radiographing stand is remote-controlled by the operation handle 42 and the monitor 43 provided at the control portion 41, and when the remote control reading portion 39 provided at the control table of the control portion 41 is turned on, it is possible to communicate with the communication circuit portion 7 of the detector unit 1 by sending and receiving radio signals. Also, the X-ray images can be displayed on the monitor 43.

Next, operations of the X-ray image taking apparatus are explained. First, the detector unit 1 of the fluoroscopic radiographing stand is rotated by 90° around the rotating shaft 3 of the detector unit 1 to have a vertical position in advance. Then, an object or patient 9 is received on the top board 10, and the detector unit 1 is returned to its original horizontal position. Next, the detector unit 1 is moved along the D directions on the supporting plate 17 by operating the operation handle 42 of the control portion 41 to allow the detector unit 1 to approach the object 9. Then, the fluoroscopying is carried out.

X-rays passing through the object 9 enter the detector unit 1. In the detector unit 1, a bias voltage is supplied to the X-ray converting layer 37 from the upper electrode 36. The TFTs 32 as the switching elements are connected to the pixel electrodes 31 arranged in a matrix shape on the active matrix board 35 and located immediately under the X-ray converting layer 37. When X-rays are irradiated, the respective switching elements as the TFTs 32 are sequentially turned on at the gate circuit 5 and signal charges accumulated in the condensers 38 of the respective pixels 30 are read at the reading circuit portion 24. The signal charges are inputted into a TV circuit (not shown) disposed in the control portion 41 through an A/D converter (not shown) from the reading circuit portion 24, so that image signals sent sequentially are processed and converted to image signals. Thus, X-ray images are displayed on the monitor 43.

The detector unit 1 is moved in the A and C directions or rotated in the head-feet directions of the object 9 around a supporting point of the C-arm 14 by operating the operation handle 42, or the top board 10 is rotated in the B directions by the rising-falling C-arm 13, so that a concerned portion of the object 9 is positioned at the center of the monitor 43. When the position is set, an image taking button of the operation handle 42 is pushed to take an image. Then, the image is stored in an storing device of the control portion 41.

Next, an operation method by receiving or sending signals through radio waves with the operation of the communication circuit portion 7 built in the detector unit 1 is explained. As mentioned above, the detector unit 1 is rotated in the vertical direction by 90° around the rotating shaft 3 in advance. Then, the object 9 is received on the top board 10, and the detector unit 1 is returned to the original horizontal position. Then, the communication circuit portion 7 is set for communication by the non-contact I/O device 8 disposed at a side surface of the detector unit 1. Through the setting of the communication circuit portion 7 and turning on the remote control reading portion 39 provided on the control table of the control portion 41, the communication circuit portion 7 of the detector unit 1 can send or receive radio signals to or from the remote control reading portion 39 with each other. Then, the X-ray images can be displayed on the monitor 34.

Also, the remote control reading portion 39 can be separated from the control portion 41 and moved to a remote place, so that the signals can be sent or received by radio waves through operation from the remote place. The remote control reading portion 39 can also be moved together with the display monitor.

Also, since the detector unit 1 can be removed from the fluoroscopic radiographing stand at the rotating shaft 3 by loosening a lock of the supporting plate 16 for supporting the detector unit 1 on the side of the fluoroscopic radiographing stand, the detector unit can be easily exchanged. Thus, the detector unit 1 can be used by attaching to another fluoroscopic radiographing stand having the same specification.

While the embodiment of the detector unit 1 having the non-contact I/O device 8 has been described, the detector unit 1 having the increased number of slide electrodes 4 without providing the non-contact I/O device 8 may be used for data transfer.

In the plane type radiation detector unit and the X-ray image taking apparatus according to the present invention structured as described above, since the rotating shaft is disposed on one end side of the small and light detector unit without a built-in power source, and the detector unit is attached to the fluoroscopic radiographing stand by the shaft, it is not required to dispose a large attaching frame for attaching a large and heavy detector cassette having a power source therein as in the prior art.

Also, since the signals can be inputted to or outputted from the detector unit and the power can be supplied thereto by providing the slide electrodes on the above-stated rotating shaft and the slip electrodes on the holding side, i.e. supporting plate, it is not required to connect by a connector and a cable as in the prior art. Thus, no cable is required, and exchange of the detector unit due to deterioration or trouble of the radiation can be easily made. Further, the apparatus can be designed nicely. Also, since it is not required to dispose a heavy power source in the detector unit, the detector unit becomes small and light.

Also, since one end side of the detector unit is provided with the rotating shaft, a space in front of the object to be tested can be widened by rotating the detector unit by 90° around the shaft. Thus, when the object or patient to be tested gets on or off the top board, the detecting unit does not cause the trouble in getting on and off. Thus, the patient can get on or off the top board safely and easily. Further, when the operator of the apparatus operates a probe or carries out an insertion examination and medical treatment by using an ultrasonic wave diagnostic device together, since the detector unit does not disturb the operation, the operator can carry out the operation precisely with an easy posture.

Since no heavy and large part, such as a power source, is built in the detector unit, the detector unit can be made small in size and light in weight, so that an attaching frame which is required in the prior art need not be attached on the side of the fluoroscopic radiographing stand. Therefore, the fluoroscopic radiographing stand is made compact and the detector unit can be quickly moved, so that the detector unit can be positioned at a concerned portion of the object to be tested.

While the invention has been explained with reference to the specific embodiments of the invention, the explanation is illustrative and the invention is limited only by the appended claims.

What is claimed is:

1. An X-ray image taking apparatus comprising:
   a supporting portion,
   an X-ray tube attached to one side of the supporting portion, and
   a plane type radiation detector unit connected to the other side of the supporting portion to be able to face the X-ray tube, said radiation detector unit including;
   an X-ray converting layer sensitive to X-rays and outputting charge signals corresponding to intensity of incident X-rays,
   an active matrix board located under the X-ray converting layer and having switching elements arranged in a matrix shape,
   a gate circuit portion having gate lines electrically connected to the switching elements for sequentially turning on the respective switching elements when signals are read,
   a reading circuit portion having reading signal lines for reading charge signals accumulated in respective pixels through reading signal lines,
   a control circuit portion electrically connected to the gate circuit portion and the reading circuit portion for controlling the same, and
   a rotating shaft disposed on one end side of the unit and rotationally attached to the supporting portion of the image taking apparatus so that the radiation detector unit can face the X-ray tube substantially perpendicularly to receive the X-rays thereon and can be rotated through the rotating shaft not to face the X-ray tube.

2. An X-ray image taking apparatus according to claim 1, wherein said rotating shaft includes a plurality of slide electrodes disposed thereon, and said supporting portion includes a plurality of slip electrodes rotatably contacting said slide electrodes.

3. An X-ray image taking apparatus according to claim 2, wherein said support portion is moved up and down relative to a frame, said radiation detector being removably attached to the support portion.

4. An X-ray image taking apparatus according to claim 1, further comprising a remote control reading portion for receiving radio output signals from an outside and sending radio control signals to the outside, said radiation detector further including a communication circuit portion for receiving the radio control signals from the remote control reading portion to control the control circuit portion and sending the radio output signals to the remote control reading portion.

5. An X-ray image taking apparatus according to claim 1, wherein said radiation detector is rotated substantially parallel to the incident X-rays from a position where the radiation detector unit faces the X-ray tube substantially perpendicularly to receive the X-rays thereon.

6. An X-ray image taking apparatus according to claim 5, further comprising a top board located between the X-ray tube and the radiation detector, said radiation detector being generally located above the top board when an X-ray image is taken and being rotatable to be located away from the top board when the X-ray image is not taken.

7. An X-ray image taking apparatus according to claim 6, further comprising a first supporting plate fixed to the supporting portion, and a second supporting plate vertically slidably attached to the first supporting plate, said radiation detector unit being rotatable attached to the second supporting plate.

* * * * *